United States Patent [19]
Waldhauer, Jr.

[11] Patent Number: 5,152,180
[45] Date of Patent: Oct. 6, 1992

[54] METHOD AND APPARATUS FOR DETECTING DISSOLUTION OF A SOLID IN A LIQUID

[75] Inventor: Charles H. Waldhauer, Jr., Glendora, Calif.

[73] Assignee: Hughes Aircraft Company, Los Angeles, Calif.

[21] Appl. No.: 612,176

[22] Filed: Nov. 13, 1990

[51] Int. Cl.⁵ ............................................. G01H 13/00
[52] U.S. Cl. .................................. 73/579; 73/602; 73/659
[58] Field of Search ............... 73/579, 602, 645, 646, 73/647, 648, 659, 590, 61 R; 366/116, 142

[56] References Cited
U.S. PATENT DOCUMENTS

| | | | |
|---|---|---|---|
| 3,576,521 | 4/1971 | Silverman | 73/646 |
| 4,327,587 | 5/1982 | Docekal et al. | 73/590 |
| 4,881,402 | 11/1989 | Markert et al. | 73/61 R |
| 5,033,321 | 7/1991 | Gerson | 73/866 |

Primary Examiner—Hezron E. Williams
Assistant Examiner—Rose M. Finley
Attorney, Agent, or Firm—Michael W. Sales; Wanda K. Denson-Low

[57] ABSTRACT

A method and apparatus for detecting completion of the dissolution of a soluble solid material in a liquid in a container. The container and its contents are excited by a wide frequency band excitation signal, causing the container and its contents to respond at a predominant frequency. The frequency response of the container and its contents is successively sampled and measured, and the respective predominant frequency response values are compared with preceding values. As the solid dissolves in the liquid, the predominant response frequency will change. Once the predominant frequency response stabilizes from sample to sample at a particular value, the dissolving process is complete. The detection method and apparatus can be used to control a motorized agitator to prevent overmixing and save energy.

11 Claims, 2 Drawing Sheets

METHOD AND APPARATUS FOR DETECTING DISSOLUTION OF A SOLID IN A LIQUID

BACKGROUND OF THE INVENTION

The present invention relates to a method and apparatus for indicating when a solid is completely dissolved in a liquid.

An agitating device is commonly used to agitate a liquid/solid mix to facilitate the complete mixture and dissolution of the solid particles in a liquid. A simple example is that of a spoon used to stir sugar into coffee or tea. Of course, there are many other such uses and examples, wherein the agitating device may be motor-driven, such as in the mixture of pharmaceuticals, coatings and various chemicals and solid reagents. Insofar as is known, the only known technique for determining when the solid has been completely dissolved is by physical inspection.

It is therefore an object of the present invention to provide a practical method and apparatus which can be used to detect when a solid has been fully dissolved in a mixture, thereby permitting the saving of energy through the prevention of overmixing the mixture, and providing a positive indication that the solid has been completely dissolved.

SUMMARY OF THE INVENTION

These and other objects and advantages are provided in accordance with the invention by a method and apparatus for detecting the completion of the dissolving of a solid into a liquid. The method comprises the steps of:

exciting the mixture of the liquid and solid with sonic excitation energy;

detecting the frequency response of the liquid and solid mixture to the excitation energy at respective sample time intervals;

determining the predominant response frequency from the detected response;

comparing the particular predominant frequency for the present sample with the predominant frequency from the previous sample; and determining that the dissolving of the solid into the liquid has been completed if there has been no change in the predominant frequency from one sample to the next.

The method can further include the steps of agitating the mixture of the liquid and the solid, and ceasing said agitation in response to the determination that the dissolving of the solid into the liquid is completed.

The step of exciting the mixture may comprise exciting the mixture with a square wave signal at a particular fundamental frequency, and the step of determining the predominant response frequency may comprise cancelling the excitation fundamental frequency component from the detected response, and determining the predominant frequency from the remaining frequency components of the detected response.

A system for determining when a solid has dissolved into a liquid comprises, in accordance with the invention, means for exciting the mixture of the liquid and solid with sonic excitation energy, means for detecting the frequency response of the mixture to the excitation energy at respective sample time intervals and generating successive response signals for each sample, and means for determining that the dissolving of the solid into the liquid has been completed when there has been no change in the predominant frequency of the response from one sample to the next. When the invention is embodied in an agitating system, the determining means can be employed to generate a "dissolve-complete" signal used to stop a power agitator device, thereby preventing overmixing and saving power.

BRIEF DESCRIPTION OF THE DRAWING

These and other features and advantages of the present invention will become more apparent from the following detailed description of an exemplary embodiment thereof, as illustrated in the accompanying drawings, in which.

DETAILED DESCRIPTION OF THE PREFERRED EMBODIMENT

The invention can first be explained using a simple example, that of stirring granules of sugar into a cup of tea or coffee. First, it will be noted that by striking the cup with a spoon prior to pouring the sugar into the cup, a sound will be produced at a particular predominant frequency or pitch. After the sugar is poured into the liquid in the cup, and as the mixture is stirred with the spoon, the predominant frequency of the resonant sound produced by the spoon against the cup will change as the sugar is dissolved into the liquid; i.e., the predominant frequency will increase. Once the sugar has fully dissolved into the liquid, the predominant frequency of the sound produced by striking the spoon against the cup will remain constant. The invention exploits this phenomenon to obtain an indication that a solid material has been dissolved into a liquid.

Figure 1:
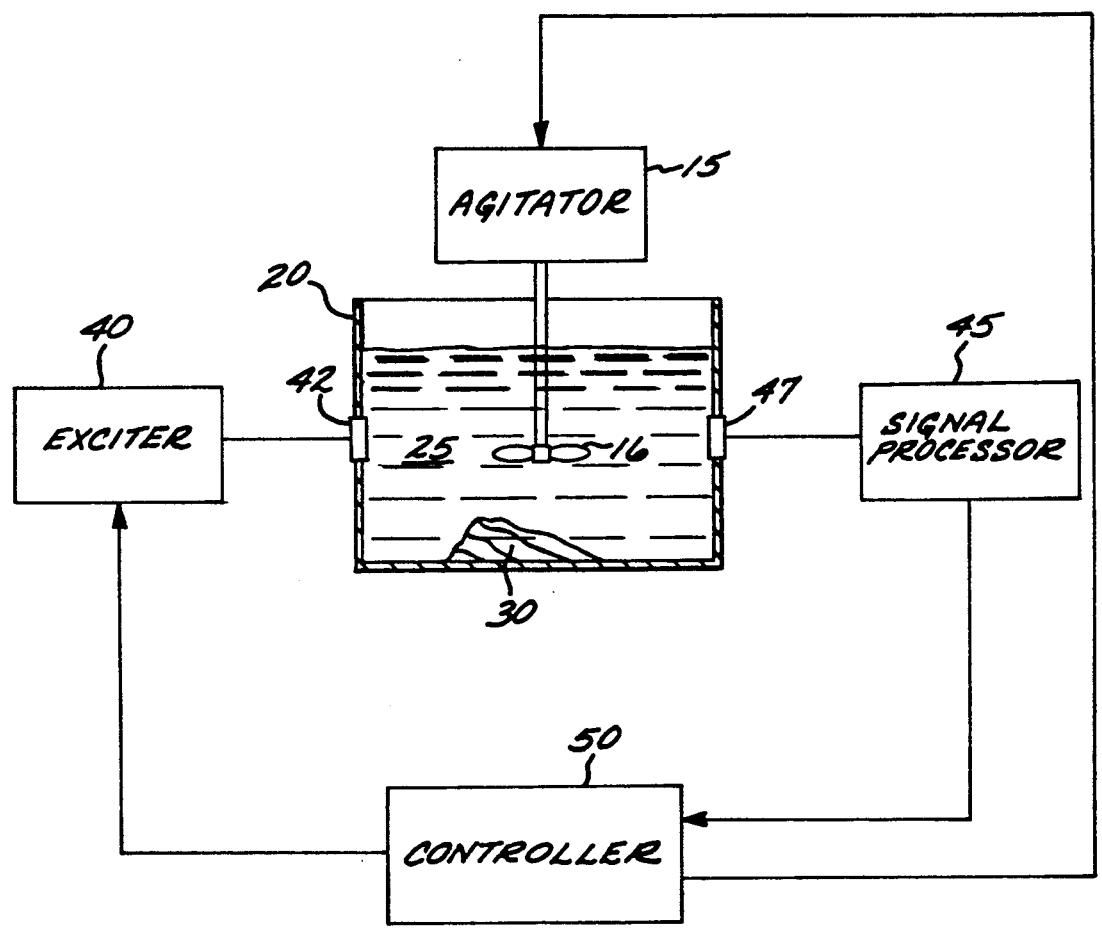
FIG. 1 is a simplified block diagram of a solubility detector system embodying the present invention.

Referring now to FIG. 1, a simplified block diagram of a solubility detection system in accordance with the invention is illustrated. A container 20 has disposed therein a quantity of a liquid 25 in which an amount of soluble solid material 30 has been placed. An agitator device 15 is provided to agitate the liquid/solid mixture. The goal for this particular application is to control the agitator device 15 so as to prevent overmixing of the mixture of the material within the container 20.

In accordance with the invention, an exciter source 40 drives a sonic transducer 42 mounted into one wall of the container 20 with a wide band excitation signal. For example, the excitation signal may be a square wave signal, comprising frequency components covering a wide frequency band; in this case the exciter 40 would comprise a square wave generator producing a square wave signal at a fundamental frequency and have many harmonic frequency components. The transducer 42 may be a vibratory-type device, similar to a "bin shaker" device commonly used to empty parts from a bin, or a microphone. In some applications, the agitator device 15 may have an excitation source mounted thereon to sufficiently excite the container and its contents so that separate exciter elements 40 and 42 are unnecessary. For example, the agitator may include an element mounted to the agitator element 16 which excites the contents of the container with frequency components over a wide frequency range.

The system further comprises a transducer 47 whose output is connected to a detector/signal processor device 45. The transducer 47 may, e.g., comprise a microphone, and provide a signal indicative of the response of the container and its contents to the excitation signal. The signal processor 45 serves the function of processing the signal from the transducer 47 to determine the predominant frequency of the response of the container and its contents to the transducer 47 output. Thus, in a particular example, the device 45 may comprise an analog-to-digital converter and a digital signal processor for analyzing the digitized transducer output, and determining the frequency component having the highest amplitude at sequential instants of time, separated by a time interval determined in accordance with the particular application and its time constants. This predominant frequency value is then sent to the controller 50 for storage and subsequent comparison with the next value. The controller 50 controls the operation of the exciter 40 and the agitator 15.

Figure 2:
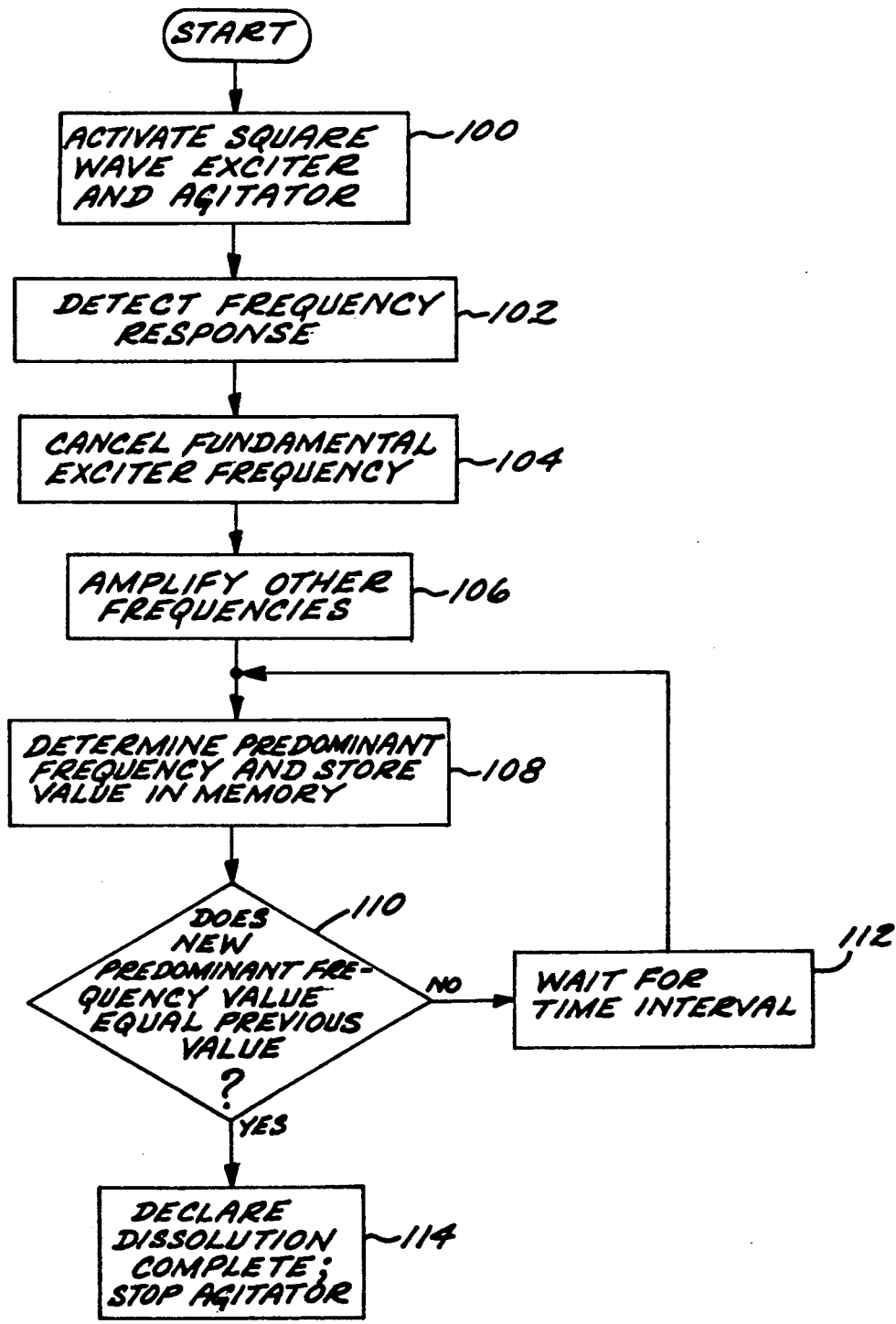
FIG. 2 is a simplified operational flow diagram illustrative of the operation of the system of FIG. 1.

The operation of the system is described in connection with the operational flow diagram of FIG. 2. Operation is commenced at step 100 with the activation of the agitator 15 and the exciter 40. At step 102, the frequency response of the container and its contents is detected by transducer 47. The signal processor 45 operates to cancel the exciter fundamental frequency from the response of the transducer 47 to provide a true frequency response for the mixed contents. This may be done by mixing the transducer output with a signal at the fundamental frequency of the exciter, or by filtering the digitized transducer output to remove the signal component at the fundamental frequency. Such digital filtering processes are well known in the digital signal processing arts. Cancellation of the fundamental frequency is necessary because otherwise the fundamental frequency component would dominate the measurement; because the fundamental frequency would be unchanging, the system would not operate properly to detect the condition that the material 30 is fully dissolved in the liquid 25. The remaining signal components are then amplified (if necessary) at step 106.

At step 108, the filtered signal is processed to determine the predominant frequency of the true frequency response of the container and its contents to the excitation. This involves determining the frequency component of the filtered transducer output having the highest amplitude in this illustrative example. This value is stored in memory, typically comprising the controller 50. The controller 50 then compares the predominant frequency value to the immediately preceding value to see if there has been any change from the last measurement of the predominant frequency. If the preceding value did not equal the present value, then operation waits for some predetermined time interval (step 112), whose value is determined in dependence on the characteristics of the particular application, and then repeats steps 108 and 110. If the present and preceding predominant frequency values are equal, this indicates that the material 30 has been fully dissolved in the liquid 25, and at step 114, dissolution is declared complete. The controller 50 can then turn off the agitator device in response to this declaration to prevent overmixing of the mixture and saving energy which would otherwise be needlessly expended.

It is understood that the above-described embodiments are merely illustrative of the possible specific embodiments which may represent principles of the present invention. The invention, for example, may find utility in mixing together two dissimilar miscible liquids, e.g., an epoxy resin and hardener. Another possible application is in urinalysis, e.g., in suspected drunken driving testing, to provide a positive indication of thorough reagent mixing. Other arrangements may readily be devised in accordance with these principles by those skilled in the art without departing from the scope and spirit of the invention.

What is claimed is:

1. A method for mixing two materials together into a solution, comprising the steps of:
   mixing the materials to form a mixture in a container;
   exciting the mixture with sonic excitation energy having a fundamental exciter frequency;
   detecting the frequency response of the mixture to the excitation energy;
   cancelling the fundamental exciter frequency from the frequency response to provide a true frequency response;
   analyzing the true frequency response to determine a predominant frequency for the mixture; and
   ceasing to mix the materials when there has been no change in the predominant frequency over time.

2. The method of claim 1 further comprising the step of determining that one material has been dissolved in the other material, said dissolving determining step including the steps of:
   comparing the predominant frequency for a present mixture sample with the predominant frequency from the previous mixture sample;
   determining that said dissolving is complete if there has been no change in said predominant frequency for the present and previous sample.

3. The method of claim 2 wherein said step of exciting the mixture comprises exciting the mixture with a square wave signal.

4. The method of claim 1 wherein said step of determining the predominant frequency comprises the step of determining which frequency component of the true frequency response has the greatest amplitude.

5. The method of claim 1 wherein said step of detecting the response to the excitation energy comprises using a microphone to detect the response.

6. The method of claim 1 further comprising the steps of agitating said mixture, and ceasing said agitation in response to the determination that said dissolving is completed.

7. A system for mixing two materials, comprising:
   means for mixing the materials to form a mixture,
   means for exciting the mixture with sonic excitation energy having a fundamental exciter frequency;
   means for detecting the frequency response of the mixture to the excitation energy at successive time intervals and generating successive response signals for each interval;
   means for cancelling the fundamental exciter frequency from the exciter frequency from the response signal to provide a true frequency response for each interval;
   means for determining a predominant response frequency from the true frequency response;
   means for ceasing mixing of the mixture when there has been no change in the predominant frequency from one sample interval to the next.

8. The system of claim 7 wherein said exciting means comprises means for exciting said mixture with a square wave signal at a particular fundamental frequency.

9. The system of claim 7 wherein said means for determining the predominant response frequency comprises means for determining which frequency component of the true frequency response has the greatest amplitude.

10. The system of claim 7 wherein said means for detecting the response to the excitation energy comprises a microphone transducer.

11. The system of claim 7 wherein said exciting means comprises a sonic transducer.

* * * * *